United States Patent [19]

Adams et al.

[11] Patent Number: 4,925,565

[45] Date of Patent: May 15, 1990

[54] PROCESS FOR EXTRACTING AND DISPOSING OF NITROPHENOLIC BY-PRODUCTS

[75] Inventors: Earl G. Adams, Grand Bay, Ala.; Robert B. Barker, Gautier, Miss.

[73] Assignee: First Chemical Corporation, Pascagoula, Miss.

[21] Appl. No.: 242,882

[22] Filed: Sep. 12, 1988

[51] Int. Cl.$^5$ ............................................. C02F 1/26
[52] U.S. Cl. ................................... 210/634; 210/909
[58] Field of Search ............... 568/757; 210/909, 634, 210/726

[56] References Cited

U.S. PATENT DOCUMENTS

| | | | |
|---|---|---|---|
| 2,812,305 | 11/1957 | Manka | 210/909 X |
| 4,401,570 | 8/1983 | Blytas et al. | 210/909 X |
| 4,418,221 | 11/1983 | Yasuda et al. | 568/757 |
| 4,597,875 | 7/1986 | Carr et al. | 210/726 X |
| 4,793,931 | 12/1988 | Stevens et al. | 210/636 |

Primary Examiner—Frank Spear
Attorney, Agent, or Firm—A. W. Breiner

[57] ABSTRACT

A process for treating nitrophenolic by-products contained in nitration waste water including the steps of solvent extraction, solvent and nitrophenolic residue recovery by distillation, and incineration of the nitrophenolic residue is disclosed. The extraction process involves the extraction of the nitrophenolic by-products from the nitration waste water utilizing a solvent in the presence of an acid at an elevated temperature and acidic pH. The extraction produces a nitrophenolic solvent solution which is subjected to a distillation to recover the solvent for reuse and produce a residue containing the nitrophenolic materials. The residue can be disposed of by incineration.

16 Claims, 2 Drawing Sheets

PROCESS FOR EXTRACTING AND DISPOSING OF NITROPHENOLIC BY-PRODUCTS

FIELD OF INVENTION

The present invention is directed to a process for treating nitrophenolic by-products contained in nitration waste water involving (1) solvent extraction of the nitrophenolic by-products from nitration waste water, (2) distillation of the solvent-nitrophenolic extract to recover the solvent for reuse and produce a residue containing the nitrophenolic by-products, and (3) incinerating the residue. The extraction process removes the nitrophenolic by-products from nitration waste water through the use of a solvent in the presence of an acid. The extraction is performed at an elevated temperature and acidic pH.

BACKGROUND OF THE INVENTION

During a nitration process to produce a desired chemical product, such as nitrotoluene or nitrobenzene, nitrophenolic by-products are produced. These by-products are separated from the desired nitrated product by washing. The by-products are then present in the wash water or waste water stream which must be disposed of without harming the environment.

There are various processes known in the art for disposing of waste water containing nitrophenolic materials. The nitrophenolic materials are usually present in the form of di- and tri-nitrophenols and di- and tri-nitrocresols. One current process for disposing of these by-products is to collect the waste water from the nitration washers in a lagoon and adjust the pH of the waste water to approximately 1.5 causing as much of the phenolic compounds as possible to precipitate. However, due to environmental concerns and the increasing number of chemical by-products which must be disposed of safely, alternative methods must be utilized.

Numerous processes are disclosed in the art for separating out nitrophenolic materials from waste water allowing for the disposal of the waste water in a conventional manner. For example, U.S. Pat. No. 4,469,561 discloses the recovery of bisphenol A and phenol from aqueous effluent streams using toluene as a solvent in a liquid-liquid extraction. Specifically, bisphenol A, phenol, and toluene are passed through an extraction column. The resulting aqueous phase, which is a toluene solution of bisphenol A and phenol, is removed and treated so that the individual components of bisphenol A, phenol, and toluene are recovered from the aqueous solution. The toluene is recycled to the extraction column for further use.

U.S. Pat. No. 4,597,875 discloses the production of dinitrotoluene with the concurrent production of nitrophenolic by-products, i.e. nitrocresols and picric acid. Prior to disposal of the waste water, the by-products are removed from the waste water. The waste water is first contacted with an alkaline material to convert the by-products to water soluble salts. An organic and aqueous phase are generated. The aqueous phase, which contains the nitrophenolic materials, is separated out and treated with an acid to convert the salts to a water insoluble material. The water-insoluble material separates into an organic phase containing the converted nitrophenolic materials and an aqueous phase containing water soluble salts. The organic phase, due to its low water content, can then be incinerated to dispose of the contaminants.

U.S. Pat. Nos. 2,808,375 and 2,812,305 disclose the purification of phenol contaminated waste waters utilizing a specified compound in combination with a solvent. The '375 and '305 patents disclose that it is known to extract undesirable phenols from waste water utilizing a solvent such as toluene. However, it is also disclosed that conventional extraction methods require five stages of extraction to remove all but a trace amount of the phenols. The '375 patent discloses the use of dehydroabietylamine and a solvent, such as toluene, in a three stage extraction process to remove the phenols from the waste water. The '305 patent discloses the use of 2-methyl-5-ethylpyridine in combination with a solvent, such as toluene, in a three stage extraction process to remove the phenols from the waste water.

U.S. Pat. No. 2,199,786 discloses the extraction of phenols from an aqueous solution utilizing liquid esters of carboxylic acid. Optionally, an additional solvent, such as toluene can be utilized with the ester.

U.S. Pat. No. 3,467,721 discloses the separation of phenols from an aqueous mixture utilizing mesityl oxide. Optionally, a second solvent, such as toluene, can be used in combination with the oxide.

U.S. Pat. Nos. 4,152,528 and 4,160,111 disclose the extraction of phenols from an aqueous mixture utilizing a combination of a ketone and a hydrocarbon compound, such as toluene, as the extracting medium.

U.S. Pat. No. 2,675,412 discloses the recovery of solvents from waste gases resulting from extraction processes. Phenol-containing waters are subjected to an extraction process. A separator then separates the water phase and the solvent containing phase. The solvent containing phase is then subjected to distillation to recover the solvent for further use. The phenols are subjected to any desired further treatment. The '412 patent does not specify the further treatment of the phenols.

U.S. Pat. No. 2,807,654 discloses the removal of phenols from waste water utilizing a solvent, such as an aromatic hydrocarbon, and a salt.

U.S. Pat. No. 4,421,649 discloses the removal of chlorinated hydrocarbon solid particles from an aqueous suspension. The suspension is acidified prior to extraction. Extraction utilizing a solvent then takes place whereby the solvent takes up the sludge from the suspension. A preferred solvent is disclosed as an aromatic petroleum fraction, such as kerosene.

The art does not disclose the treatment of nitrophenolic by-products utilizing an extraction process including the concurrent use of a solvent with an acid as described in the present invention. The extraction of nitrophenolic by-products of the present invention is both efficient and economical. The present invention additionally provides for the recovery of the solvent while placing the nitrophenolic by-products in a form suitable for environmentally safe disposal.

OBJECTS OF THE INVENTION

A primary object of the present invention is to provide a process for the treatment of nitrophenolic by-products utilizing solvent extraction to remove the by-products from waste water, distillation to recover the solvent for reuse and to produce a residue containing the nitrophenolic by-products, and incinerating the residue.

A further primary object of the present invention is to provide a process for the treatment of nitrophenolic by-products from waste waters involving the extraction of the by-products from the waste water utilizing a solvent concurrently with an acid at an elevated temperature and acidic pH.

A further primary object of the present invention is to provide a process for the treatment of nitrophenolic by-products from waste waters utilizing solvent extraction to remove the by-products from the waste water followed by recovery and reuse of the solvent.

A further primary object of the present invention is to provide a process for treating nitrophenolic by-products contained in nitration waste waters which is efficient and economical.

GENERAL DESCRIPTION OF THE INVENTION

The present invention provides an economical and efficient process of treating and disposing of the contaminant containing waste water, also known as "red water", resulting from the washing of nitrated products in chemical plants to remove oxidation by-products produced during the nitration process. These by-products, which make up the contaminants in the waste water, are mainly nitrophenolic materials such as di- and tri-nitrophenols and di- and tri-nitrocresols. The process of the invention utilizes solvent extraction of the waste water to provide for the collection of an organic phase containing the solvent and nitrophenolic by-products. The aqueous phase, after extraction, is essentially contaminant free waste water. This waste water is then subjected to steam stripping and carbon adsorption to insure that the waste water is free of trace amounts of contaminants so that the waste water can be disposed of in any conventional manner.

The organic phase is fed or transported to a distillation unit to recover most of the solvent utilized in the extraction process and recycle the solvent for further use in the extraction unit. At the same time that recovery of the solvent is being carried out, the distillation operation produces a residue stream containing concentrated nitrophenolic materials. This residue is suitable for disposal by incineration.

The process of the present invention results in the reduction of the cost of treating the waste water by recovering and reusing about 90% of the solvent used in the extraction process. Additionally, due to the low water content of the nitrophenolic distillation residue, the nitrophenolic by-products can be incinerated under nonintensive energy conditions.

An example of a nitration process which results in the production of a waste water stream containing the nitrophenolic by-products of dinitrophenol and picric acid, is the nitration of benzene with nitric acid in the presence of sulfuric acid to produce nitrobenzene and the above-described by-products. In the production of mononitrobenzene, the specific nitrophenolic by-products which can result include 2,6-dinitrophenol; 2,4-dinitrophenol; and picric acid. In the production of mononitrotoluene, specific nitrophenolic by-products which can be produced include 4,6-dinitro-o-cresol and 2,6-dinitro-p-cresol.

Following the nitration process, the nitrophenolic by-products are separated from the nitrated product by washing. A base, such as sodium hydroxide, is typically utilized to wash the nitrated product. The nitrated phenols are organic acids which vary in acidity from the acidity of carbonated water to being more acidic than phosphoric acid. These acids have a high solubility in nitrated aromatics and a low solubility in water. When a base is reacted with these acids, a salt is formed which is nearly insoluble in organics and very soluble in water. By utilizing countercurrent extraction, these salts can be washed from the nitrated product.

Following the washing of the nitrated product to remove the by-products, the wash water is reacted with an acid to regenerate the free nitrated phenols. Since the nitrated phenols are only slightly soluble in acid water, the nitrophenolic materials precipitate. This precipitated nitrophenolic material is then subjected to the process of the present invention. The precipitated phenols are dissolved in a solvent in the presence of an acid to remove the nitrophenolic by-products from the waste water.

The nitration wash water stream or waste water is extracted utilizing conventional extraction means. Preferably, three extraction stages are employed using commercially available extractors, such as a Karr extraction column. Alternatively, a series of mixer/settlers can be utilized to provide three stages of extraction. The use of multiple stages insures the separation and removal of all but trace amounts of the nitrophenolic by-products. Most preferably, due to variations in the feed composition and possible pH swings, four stages of extraction are utilized to give optimum results. The extra stage allows for the running of the extraction unit at higher rates than optimum. Under these conditions if a mixer-settler provides less than a true stage, the extra stage will compensate for the lesser stage or stages in the removal of the nitrophenolic materials.

The most important variable in the extraction process is the control of the pH of the waste water. When the pH of the water is above the point at which ionization of the by-product compounds occur, very little of those compounds will be removed.

In order to control the pH of the extraction, a large amount of a strong acid, such as sulfuric acid, is utilized to maintain the desired pH. The preferred pH is within the range of from 1.0 to 1.2. The acid is charged into the extraction unit concurrently with the solvent. Acidification of the waste stream prior to extraction is not necessary. Other acids suitable for use include phosphoric acid, hydrochloric acid, and other mineral acids.

Various solvents are suitable for use in the extraction process of the present invention. Although metaisobutylketone (MIBK) has been found to be a good all around solvent, it is not preferred due to its ability to form peroxides. The preferred solvents are toluene and benzene which have been found to be about equal to each other. Orthonitrotoluene and nitrobenzene can also be used as the solvent.

The suitability of a particular solvent depends upon the solubility of the by-product in the solvent. To be a suitable solvent, the by-product must be soluble in the solvent within a solubility range of from about 10 wt. %. to being soluble in all proportions. Additionally, the selected solvent should have limited water solubility. The solubility of nitrobenzene (MNB), o-nitrotoluene (O-MNT), and toluene with respect to picric acid, 2,4-dinitrophenol (2,4-DNP), and 2,6-dinitro-p-cresol (2,6-DNPC), are set forth in Table I.

TABLE I

| Solvent | Temperature(°F.) | WT % SOLUBLE IN SOLVENT | | |
|---------|------------------|-------------------------|---|---|
| | | 2,4-DNP | Picric acid | 2,6-DNPC |
| O-MNT | 70 | 13.5 | 33.5 | — |
| | 100 | 17.0 | 41.0 | 21.0 |
| | 140 | 35.5 | 39.0 | 75.0 |

TABLE I-continued

| Solvent | Temperature(°F.) | WT % SOLUBLE IN SOLVENT | | |
|---|---|---|---|---|
| | | 2,4-DNP | Picric acid | 2,6-DNPC |
| MNB | 70 | 18.0 | 33.5 | 46.0 |
| | 100 | 19.5 | 34.5 | 60.0 |
| | 140 | 43.0 | 51.5 | 75.0 |
| Toluene | 70 | 9.0 | 21.5 | 48.5 |
| | 100 | 21.0 | 34.5 | 56.0 |
| | 140 | 36.5 | 44.5 | 76.5 |

For the purpose of discussion and without limiting the scope of the invention, the process of the invention will be described in terms of utilizing toluene as the solvent.

The extraction process was found to remove the nitrated phenols to less than 100 ppm under ideal conditions. In all cases, it has been found that the nitrophenolic materials are extracted better at lower pHs and at lower water to solvent ratios.

The solvent to water ratio is adjusted based on the feed composition and the raffinate quality desired. The raffinate is the extraction product containing minimal amounts of nitrophenolic materials. More specifically, the water to solvent ratio is determined experimentally so that the maximum concentration obtained is a 10% concentration of phenolic material in organic solvent.

A raffinate containing less than 100 ppm of dissolved nitrophenolic materials is desired. The distribution coefficient for the toluene-water/by-product system is approximately 50/1 at optimum pH or lower. At a coefficient of 10/1 and a water to solvent ratio of 5/1, four stages will reduce the by-products present from 7500 ppm to approximately 100 ppm.

The by-products can be concentrated in the toluene phase, called the extract, to at least 10%. To avoid possible by-product precipitation, the extract is maintained at approximately the same temperature as used during the extraction process. The extract will present no danger from instability if it is not overheated resulting in the evaporation of the toluene. Samples containing approximately 50% toluene and 50% extracted by-products have been found to have thermal stability and be safe from detonation.

For the extraction of the waste water resulting from the production of nitrobenzene, a suitable solvent to water ratio is 10/1. When mononitrotoluene wash water is subjected to extraction according to the present invention, a larger amount of solvent is required, i.e. in the range of from 4/1.

The extraction process of this invention will extract the nitrophenols at a higher throughput and higher water to toluene ratio than is possible when extracting nitrocresols from mononitrotoluene wash water. The mononitrotoluene wash water tends to form an extraction rag and cause phase separation problems unless a water to toluene ratio of 4/1 or less is utilized. When mononitrotoluene wash water is mixed with mononitrobenzene wash water, the extraction is facilitated and no problems occur. A water to toluene ratio of from 5/1 to 10/1 provides suitable extraction when the two streams of wash waters are mixed.

In order to avoid the precipitation of picric acid during wash water extraction, an excess of solvent is commercially required. The use of an excess of solvent, however, is avoided by the process of the present invention by maintaining an elevated temperature during the extraction process, preferably in the range of from about 140° F. to 150° F. Further, the use of an elevated temperature allows for the utilization of a higher water to solvent ratio. No precipitation occurs in the process at the elevated temperature.

Following the extraction process, the solvent utilized can be recovered leaving a nitrophenolic material containing residue. The phenolic toluene stream from the extraction unit can be fed directly to the solvent recovery unit or depending on the physical lay-out of the plant, the phenolic toluene solution can be fed into a collection container at the end of the extraction process, such as a drum, and transported to the solvent recovery unit where it will be charged into a still. The solvent recovery unit distills off approximately 90% of the toluene. The recovered toluene can be reused in the extraction process. The residue stream remaining after the distilling off of the solvent contains approximately 50% toluene and 50% nitrophenolic materials. The recovered residue is in a form suitable for incineration.

PRESENTLY PREFERRED EMBODIMENT OF THE INVENTION

Figure 1:
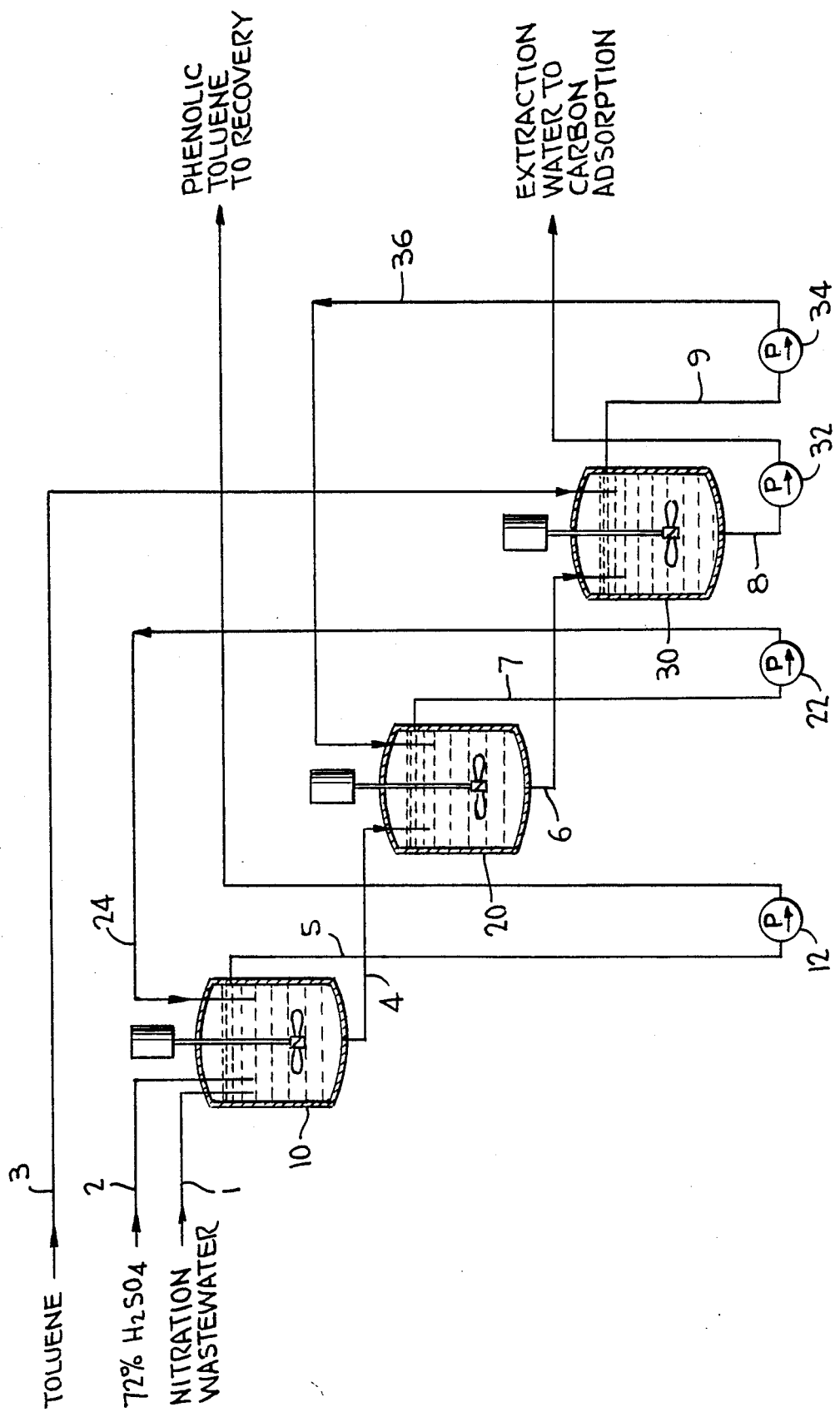
FIG. 1 is a schematic of one preferred embodiment of the extraction process of the present invention.

A presently preferred embodiment of the nitration waste water extraction process is schematically shown in FIG. 1. Table II, infra, sets forth the component makeup of the streams shown in FIG. 1 as well as the pH and temperature of the components at various points in the extraction process. The stream numbers 1 through 9 denoted in FIG. 1 correspond to the stream numbers set forth in Table II. The nitration waste water, containing nitrophenolic by-products, is mixed with toluene and 72% sulfuric acid. The sulfuric acid lowers the pH of the waste water to approximately 1.0-1.2. The waste water is extracted utilizing toluene in three stirred mixer/settlers, as shown in FIG. 1. As discussed above, four mixing/settling stages can be utilized to allow for the running of the extraction unit at a higher rate than optimum with only three extractors to compensate for when a mixer/settler provides less than a true stage.

A settling time of approximately 3 to 5 minutes is provided between the stages to allow for the separation of the phases. Separation improves with the elevation of temperature. The process is preferably run at an elevated temperature within the range of from about 140° F. to 150° F. The addition of a strong aqueous sulfuric acid solution heats the approximate 100° F. water to approximately 140° F. to 150° F. when the acid is diluted and neutralizes the mixture and when the acid reacts with any sodium hydroxide or phenol salts present in the waste water due to the nitration process. Additionally, the elevated temperature allows for a higher water to solvent ratio and increases the distribution coefficient of the materials.

Referring to FIG. 1, the initial streams are the nitration waste water 1, 72% sulfuric acid 2, and toluene 3. The first extractor tank 10 is fed with nitration waste water 1 and 72% sulfuric acid 2. The toluene charged to the first extractor tank 10 pumped with pump 22 through line 24 is the toluene recovered from the second extractor tank 20. The toluene charged into the second extractor tank 20 pumped with pump 34 through line 36 is the toluene recovered from the third extractor tank 30. The toluene from stream 3 is charged into the third extractor tank 30. The phenolic-toluene mixture which is fed to the solvent recovery unit is the material discharged from the first extractor tank 10 through line 5, utilizing pump 12.

The raffinate from the third extraction unit 30 is pumped by pump 32 through line 8 to a treatment center where it is subjected to steam stripping and carbon adsorption according to conventionally known methods to further insure the removal of solvent from the water prior to disposal of the water.

As apparent from FIG. 1 and as shown in Table II, the pure toluene is fed to the third extraction unit 30 and, after picking up the final traces of phenolic components from the raffinate, is pumped to the second extraction unit 20 where it picks up significant amounts of phenolic compounds from the raffinate of extractor unit 20 before it is pumped to the first extraction unit 10. The solvent/phenolic mixture leaving the first extraction unit through line 5 contains substantially all of the phenolic waste products of the original waste water.

Also, as seen from Table II, the extract from first extractor 10 contains significant amounts of the phenolic waste product; whereas the extract fed through line 6 to extractor unit 30 contains substantially less of the phenolic by-product. The raffinate from extractor unit 30 contains only trace amounts of the phenolic by-products. The countercurrent flow of solvent, accordingly, provides for the most efficient utilization of the solvent.

then fed from the receiver 80 to a storage container 90 pending further use.

The "bottoms" or residue from the distillation process are fed through an outlet to a collection vessel. The residue collected on the completion of the solvent recovery can then be transported to a suitable incineration unit for disposal.

The distillation performed to recover the solvent utilized in the extraction process and the nitrophenolic by-products is carried out using conventional distillation means. The distillation performed during the solvent recovery process is preferably carried out at a reduced pressure, i.e. 20 to 25 mm in Hg, and at a temperature in the range of from about 180° F. to 190° F. with one to five stages of rectification and minimum reflux.

The separated nitrophenolic materials should not be recovered as a solid because handling of the materials is more difficult. It has been found that the nitrophenolic residue from the recovery unit will remain molten at temperatures of around 140° F. and accordingly, this is the approximate lowest temperature at which the distillation residue should be handled. The residue is generally completely melted at approximately 179° F. to 184° F.

The incineration of the residue can be carried out according to any conventionally known process.

As will be apparent to one skilled in the art, various modifications can be made within the scope of the aforesaid description. Such modifications being within the ability of one skilled in the art form a part of the

TABLE II

| COMPONENT | STREAM NO. | | | | | | | | |
|---|---|---|---|---|---|---|---|---|---|
| | 1 LBS/HR | 2 LBS/HR | 3 LBS/HR | 4 LBS/HR | 5 LBS/HR | 6 LBS/HR | 7 LBS/HR | 8 LBS/HR | 9 LBS/HR |
| WATER | 9186.0 | 228.2 | 0 | 9186.0 | 0 | 9186.0 | 0 | 9414.2 | 0 |
| 2,4-DNP | 45.0 | 0 | 0 | 4.8 | 44.9 | 0.5 | 18.4 | 0.1 | 0.4 |
| PICRIC ACID | 76.0 | 0 | 0 | 19.3 | 75.1 | 4.9 | 18.4 | 0.9 | 4.0 |
| TOLUENE | 0 | 0 | 1128.0 | 0 | 1128.0 | 0 | 1128.0 | 0 | 1128.0 |
| $H_2SO_4$ | 0 | 586.8 | 0 | 815.0 | 0 | 815.0 | 0 | 586.8 | 0 |
| TOTAL | 9307.0 | 815.0 | 1128.0 | 10025.1 | 1248.0 | 10025.1 | 1151.1 | 10002.0 | 1132.4 |
| pH | 11 | 1 | — | 1.2 | 1.2 | 1 | 1 | 1 | 1 |
| TEMP (°F.) | 100 | 70 | 70 | 150 | 150 | 140 | 140 | 130 | 130 |

Figure 2:
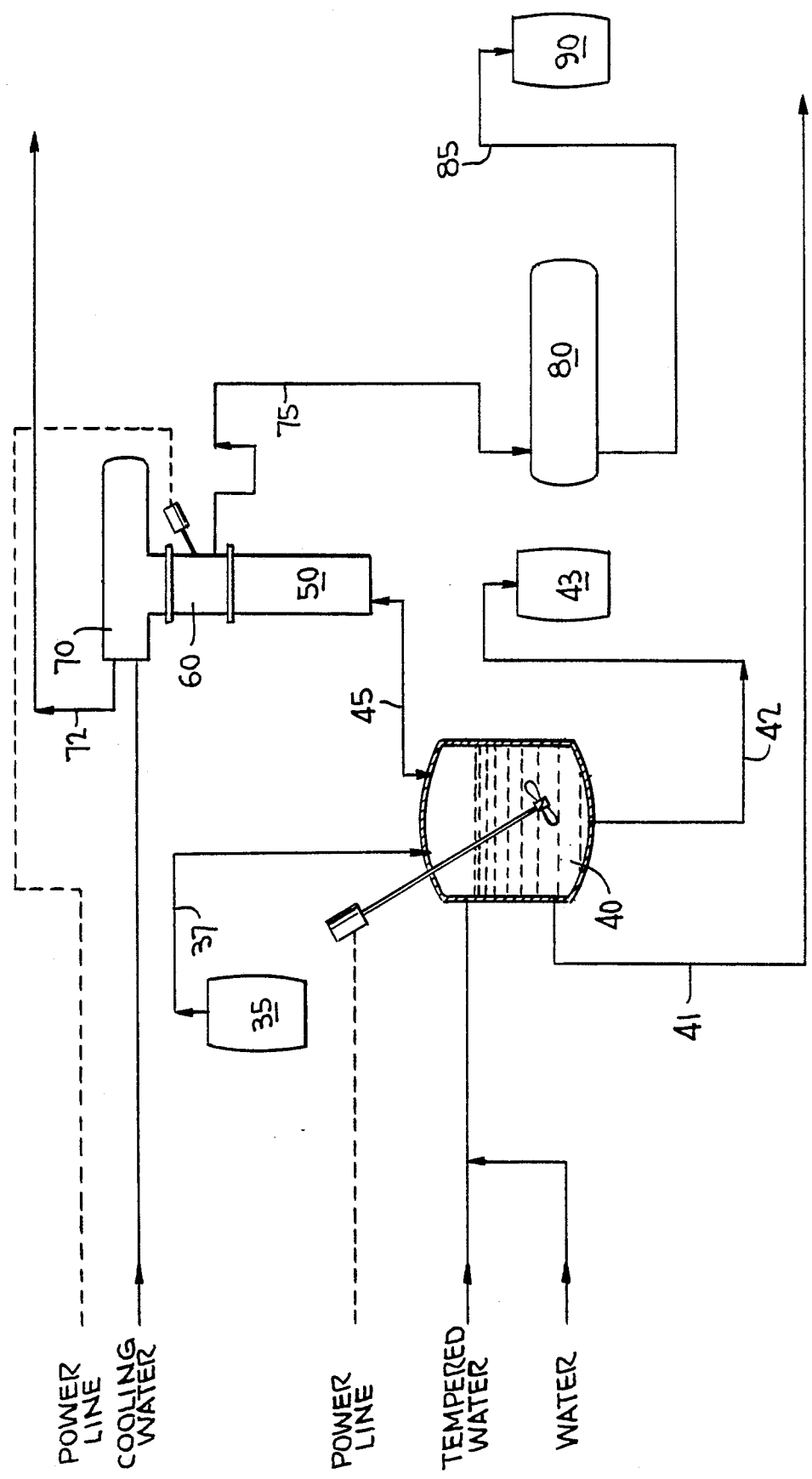
FIG. 2 is a schematic of one preferred embodiment of the solvent recovery process of the present invention.

With reference to the preferred solvent recovery process shown in FIG. 2, the phenolic toluene stream 37 is charged from container 35 into a stirred jacketed reactor 40 which is used as a batch distillation pot. From the reactor, line 45 feeds the vapor stream, which contains toluene, nitrobenzene, and nitrophenols, to distillation column 50 which separates the volatile compounds during distillation. Additionally, line 45 returns the condensate from the distillation column to the distillation pot 40. The distillation process is preferably vacuum distillation. The residue is fed from the reactor 40 through line 42 into a collection container 43. Line 41 is an outlet for the tempered water.

A reflux splitter 60 operates in conjunction with the distillation column 50 to provide a reflux stream to the column. A condensor 70 also operates in conjunction with the distillation column 50. The condensor 70 condenses the vapors from the column and provides a liquid stream to the reflux splitter. Line 72 removes noncondensable vapors from the condenser 70. Following distillation, the toluene containing overhead distillation product is fed through line 75 to a product receiver 80 which serves as a collection vessel. The toluene 85 is present invention and are embraced by the appended claims.

It is claimed:

1. A process of disposing of nitrophenolic by-products contained in nitration waste water comprising (1) extracting said nitrophenolic by-products from nitration waste water by mixing said nitration waste water with a solvent and an acid to provide a mixture having an acidic pH; heating said mixture to an elevated temperature; subjecting said mixture to extraction at said elevated temperature and acidic pH to provide a solvent solution containing said nitrophenolic by-products, (2) subjecting said solvent solution containing said nitrophenolic by-products to distillation to recover said solvent from said solvent solution and produce a residue containing said nitrophenolic by-products and (3) incinerating said residue.

2. The process according to claim 1 wherein said solvent is selected from the group consisting of toluene, benzene, o-nitrotoluene and nitrobenzene.

3. The process according to claim 1 wherein said acid is selected from the group consisting of sulfuric acid, phosphoric acid and hydrochloric acid.

4. The process according to claim 1 wherein said elevated temperature is within the range of from about 140° F. to 150° F.

5. The process according to claim 1 wherein said acidic pH of said mixture is in the range of from 1.0 to 1.2.

6. A process for extracting nitrophenolic by-products from nitration waste water comprising (1) mixing said nitration waste water with a solvent for said nitrophenolic by-products and an acid to provide a mixture having a pH in the acidic range and at a pH at which ionization of said by-products does not occur and (2) extracting a solvent solution containing said nitrophenolic by-products from said waste water at said pH in the acidic range.

7. The process according to claim 6 wherein said solvent is selected from the group consisting of toluene, benzene, o-nitrotoluene and nitrobenzene.

8. The process according to claim 6 wherein said acid is selected from the group consisting of sulfuric acid, phosphoric acid and hydrochloric acid.

9. The process according to claim 6 wherein said mixture is heated to an elevated temperature.

10. The process according to claim 9 wherein said elevated temperature is a temperature within the range of from about 140° F. to 150° F.

11. The process according to claim 6 wherein said acidic pH of said mixture is from 1.0 to 1.2.

12. A process of recovering nitrophenolic by-products contained in nitration waste water and recovering a solvent which is utilized in recovering said nitrophenolic by-products comprising (1) extracting said nitrophenolic by-products from nitration waste water by mixing said nitration waste water with a solvent and an acid to provide a mixture having a pH in the acid range, heating said mixture to an elevated temperature, and subjecting said mixture to extraction at said elevated temperature and acidic pH to provide a solvent solution containing said nitrophenolic by-products, and (2) subjecting said solvent solution containing said nitrophenolic by-products to distillation to recover said solvent from said solvent solution and produce a residue containing said nitrophenolic by-products.

13. The process according to claim 12 wherein said solvent is selected from the group consisting of toluene, benzene, o-nitrotoluene and nitrobenzene.

14. The process according to claim 12 wherein said acid is selected from the group consisting of sulfuric acid, phosphoric acid and hydrochloric acid.

15. The process according to claim 12 wherein said elevated temperature is within the range of from about 140° F. to 150° F.

16. The process according to claim 12 wherein said acidic pH of said mixture is in the range of from 1.0 to 1.2.

* * * * *